(12) United States Patent
Cresci (10) Patent No.: US 11,491,192 B2
(45) Date of Patent: Nov. 8, 2022

(54) TREATMENT AND PREVENTION OF PATHOGENIC BACTERIAL OVERGROWTH USING BUTYRATE-PRODUCING BACTERIA

(71) Applicant: THE CLEVELAND CLINIC FOUNDATION, Cleveland, OH (US)

(72) Inventor: Gail Cresci, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

(21) Appl. No.: 16/960,372

(22) PCT Filed: Jan. 9, 2019

(86) PCT No.: PCT/US2019/012838
§ 371 (c)(1),
(2) Date: Jul. 7, 2020

(87) PCT Pub. No.: WO2019/139943
PCT Pub. Date: Jul. 18, 2019

(65) Prior Publication Data
US 2021/0060087 A1 Mar. 4, 2021

Related U.S. Application Data

(60) Provisional application No. 62/615,124, filed on Jan. 9, 2018.

(51) Int. Cl.
| | | |
|---|---|---|
| A61K 35/74 | (2015.01) | |
| A61P 31/04 | (2006.01) | |
| A61P 1/00 | (2006.01) | |
| A61K 31/718 | (2006.01) | |
| A61K 35/00 | (2006.01) | |

(52) U.S. Cl.
CPC ............ *A61K 35/74* (2013.01); *A61K 31/718* (2013.01); *A61P 1/00* (2018.01); *A61P 31/04* (2018.01); *A61K 2035/115* (2013.01)

(58) Field of Classification Search
None
See application file for complete search history.

(56) References Cited

U.S. PATENT DOCUMENTS

| | | |
|---|---|---|
| 2016/0000838 A1 | 1/2016 | Harmsen et al. |
| 2016/0022592 A1 | 1/2016 | Kabadi et al. |

FOREIGN PATENT DOCUMENTS

| | | | | |
|---|---|---|---|---|
| WO | WO-2014152338 A1 | * | 9/2014 | ............ A61K 9/4816 |
| WO | 2017/072278 A1 | | 5/2017 | |

OTHER PUBLICATIONS

Acar (Clin Microbiol Infection, 3:P395-396, 1997).*
Boothe (Merk Veterinary Manual, Aminoglycosides, pp. 1-6, 2016).*
Popescu et al., BMC Infect Dis, 13(Suppl 1):O14, 2013.*
Giang et al., J. Young Pharm, 2:190-195, 2010.*
Wikipedia, "Broad-spectrum antibiotic", https://en.wikipedia.org/wiki/Broad-spectrum_antibiotic, last accessed Jan. 22, 2021.
PCT International Search Report and Written Opinion for corresponding International Application Serial No. PCT/US2019/012838, dated May 8, 2019, pp. 1-8.
Cresci G, Nagy LE, Ganapathy V. Lactobacillus GG and tributyrin supplementation reduce antibiotic-induced intestinal injury. JPEN J Parenter Enteral Nutr. Nov. 2013;37(6):763-74. doi: 10.1177/0148607113486809. Epub Apr. 29, 2013. PMID: 23630018; PMCID: PMC3818407.
Cresci GA, Bush K, Nagy LE. Tributyrin supplementation protects mice from acute ethanol-induced gut injury. Alcohol Clin Exp Res. Jun. 2014;38(6):1489-501. doi: 10.1111/acer.12428. Epub May 3, 20140. PMID: 24890666 PMCID: PMC4185400.
Cresci GAM, Mayor PC, Thompson SA. Effect of butyrate and Lactobacillus GG on a butyrate receptor and transporter during Campylobacter jejuni exposure. FEMS Microbiol Lett. Mar. 1, 2017;364(6):fnx046. doi: 10.1093/femsle/fnx046. PMID: 28333199; PMCID: PMC5399911.
Cresci, Gail A., et al. "Prophylactic tributyrin treatment mitigates chronic-binge ethanol-induced intestinal barrier and liver injury." Journal of gaslioenterology and hepatology 32.9 (2017): 1587-1597.
Roychowdhury, Sanjoy, et al. "Faecalibacterium prausnitzii and a prebiotic protect intestinal health in a mouse model of antibiotic and Clostridium difficile exposure." Journal of Parenteral and Enteral Nutrition 42.7 (2018) 1156-1167.
Zhang, Shanshan, et al. "Cost of hospital management of Clostridium difficile infection in United States—a meta-analysis and modelling study." BMC infectious diseases 16.1 (2016): 447.
Sehulster Lynne, et al., "Guidelines for Environmental Infection Control in Health-Care Facilities", https://www.cdc.gov/mmwr/preview/mmwrhtml/rr5210a1.htm?CDC_AA_refVal=https%3A%2F%2Fwww.cdc.gov%2Fhai%2Forganisms%2Fcdiff%2Fcdiff_excerpt.html, last accessed Jan. 22, 2021.
Lopetuso, Loris R., et al. "Commensal Clostridia: leading players in the maintenance of gut homeostasis." Gut pathogens 5.1 (2013): 23.
Scott, Karen P., et al. "Prebiotic stimulation of human colonic butyrate-producing bacteria and bifidobacteria, in vitro." FEMS microbiology ecology 87.1 (2014): 30-40.
Backhed, Fredrik, et al. "Host-bacterial mutualism in the human intestine." science 307.5717 (2005): 1915-1920.
Hooper, Lora V., Tore Midtvedt, and Jeffiey I. Gordon. "How host-microbial interactions shape the nutrient environment of the mammalian intestine." Annual review of nutrition 22.1 (2002): 283-307.

(Continued)

*Primary Examiner* — Brian Gangle
(74) *Attorney, Agent, or Firm* — Tarolli, Sundheim, Covell & Tummino LLP (57) ABSTRACT

A method of treating or preventing overgrowth by pathogenic bacteria in a subject deficient in butyrate and/or butyrate-producing bacteria in their gut microbiota by administering a therapeutically effective amount of a butyrate-producing bacteria to the subject is described. A prebiotic can be included with the butyrate-producing bacteria. Overgrowth by pathogenic bacteria is commonly caused by antibiotic administration.

15 Claims, 6 Drawing Sheets

(56) References Cited

OTHER PUBLICATIONS

Brandt, Lawrence J., et al. "Long-Term Follow-Up of Colonoscopic Fecal Microbiota Transplant for RecurrentClostridium difficileInfection." American Journal of Gastroenterology 107.7 (2012): 1079-1087.

Theriot, Casey M., et al. "Antibiotic-induced shifts in the mouse gut microbiome and metabolome increase susceptibility to Clostridium difficile infection." Nature communications 5 (2014): 3114.

Antharam, Vijay C., et al. "Intestinal dysbiosis and depletion of butyrogenic bacteria in Clostridium difficile infection and nosocomial diarrhea." Journal of clinical microbiology 51.9 (2013): 2884-2892.

Lawley, Trevor D., et al. "Targeted restoration of the intestinal microbiota with a simple, defined bacteriotherapy resolves relapsing Clostridium difficile disease in mice." PLoS Pathog 8.10 (2012): e1002995.

Pryde, Susan E., et al. "The microbiology of butyrate formation in the human colon." FEMS microbiology letters 217.2 (2002): 133-139.

Cummings, John H., George T. Macfarlane, and Hans N. Englyst. "Prebiotic digestion and fermentation." The American journal of clinical nutrition 73.2 (2001): 415s-420s.

Velazquez, Omaida C., Howard M. Lederer, and John L. Rombeau. "Butyrate and the colonocyte." Digestive diseases and sciences 41.4 (1996): 727-739.

Thangaraju, Muthusamy, et al. "GPR109A is a G-protein-coupled receptor for the bacterial fermentation product butyrate and functions as a tumor suppressor in colon." Cancer research 69.7 (2009): 2826-2832.

Binder, Henry J. "Role of colonic short-chain fatty acid transport in diarrhea." Annual review of physiology 72 (2010): 297-313.

Ploger, Svenja, et al. "Microbial butyrate and its role for barrier function in the gasliointestinal tract." Annals of the New York academy of sciences 1258.1 (2012): 52-59.

Inan, Mehmet Sait, et al. "The luminal short-chain fatty acid butyrate modulates NF-?B activity in a human colonic epithelial cell line." Gastroenterology 118.4 (2000): 724-734.

Hass, R. A. L. F., et al. "Lack of butyrate is associated with induction of Bax and subsequent apoptosis in the proximal colon of guinea pig." Gaslioenterology 112.3 (1997): 875-881.

Hill, Colin, et al. "Expert consensus document: The International Scientific Association for Probiotics and Prebiotics consensus statement on the scope and appropriate use of the term probiotic." Nature reviews Gaslioenterology & hepatology 11.8 (2014): 506.

Miquel, S., et al. "Faecalibacterium prausnitzii and human intestinal health." Current opinion in microbiology 16.3 (2013): 255-261.

U.S. Environmental Protection Agency Office of Pesticide Programs, Standard Operating Procedure for Production of Spores of Clostridium difficile for Use in the Efficacy Evaluation of Antimicrobial Agents, SOP No. MB-28-04, Office of Pesticide Programs, Microbiology Laboratory, Environmental Science Center, 41 Ft. Meade, MD, Jun. 19, 2014.

Duncan SH, Hold GL, Harmsen HJM, Stewart CS, Flint HJ. Growth requirements and fermentation products of Fusobacterium prausnitzii, and a proposal to reclassify it as Faecalibacterium prausnitzii gen. nov., comb. nov. Int J Syst Evol Microbiol. Nov. 2002;52(Pt6):2141-2146. doi: 10.1099/00207713-52-6-2141. PMID: 12508881.

Belenguer, Alvaro, et al. "Two routes of metabolic cross-feeding between Bifidobacterium adolescentis and butyrate-producing anaerobes from the human gut." Applied and environmental microbiology 72.5 (2006): 3593-3599.

National Committee for Clinical Laboratory Standards. Methods for dilution antimicrobial susceptibility tests for bacteria that grow anaerobically, 5th ed. Approved standard M7-A5. National Committee for Clinical Laboratory Standards, Wayne, PA, 2000.

Pultz, Nicole J., and Curtis J. Donskey. "Effect of antibiotic treatment on growth of and toxin production by Clostridium difficile in the cecal contents of mice." Antimicrobial agents and chemotherapy 49.8 (2005): 3529-3532.

Cresci, Gail A., et al. "Colonic gene expression in conventional and germ-free mice with a focus on the butyrate receptor GPR109A and the butyrate transporter SLC5A8." Journal of Gastrointestinal Surgery 14.3 (2010): 449-461.

Engevik, Melinda A., et al. "Human Clostridium difficile infection: inhibition of NHE3 and microbiota piolile." American Journal of Physiology-Gastrointestinal and Liver Physiology 308.6 (2015): G497-G509.

Tao, Liang, et al. "Frizzled proteins are colonic epithelial receptors for C. difficile toxin B." Nature 538.7625 (2016): 350-355.

Staley, Christopher, et al. "Complete microbiota engraftment is not essential for recovery from recurrent Clostridium difficile infection following fecal microbiota transplantation." MBio 7.6 (2016).

Buffie, Charlie G., et al. "Profound alterations of intestinal microbiota following a single dose of clindamycin results in sustained susceptibility to Clostridium difficile-induced colitis." Infection and immunity 80.1 (2012): 62-73.

Hayashi, Hisayoshi, et al. "Inhibition and redistribution of NHE3, the apical Na+/H+ exchanger, by Clostridium difficile toxin B." The Journal of general physiology 123.5 (2004): 491-504.

Sun, Xingmin, and Simon A. Hirota. "The roles of host and pathogen factors and the innate immune response in the pathogenesis of Clostridium difficile infection." Molecular immunology 63.2 (2015): 193-202.

Laval, L., et al. "Lactobacillus rhamnosus CNCM I-3690 and the commensal bacterium Faecalibacterium prausnitzii A2-165 exhibit similar protective effects to induced barrier hyper-permeability in mice." Gut microbes 6.1 (2015): 1-9.

El Feghaly, Rana E., et al. "Markers of intestinal inflammation, not bacterial burden, correlate with clinical outcomes in Clostridium difficile infection." Clinical infectious diseases 56.12 (2013): 1713-1721.

Hasegawa, Mizuho, et al. "Nucleotide-binding oligomerization domain 1 mediates recognition of Clostridium difficile and induces neutrophil recruitment and protection against the pathogen." The Journal of Immunology 186.8 (2011) 4872-4880.

Ryan, Anthony, et al. "A role for TLR4 in Clostridium difficile infection and the recognition of surface layer proteins." PLoS Pathog 7.6 (2011): e1002076.

Jarchum, Irene, et al. "Critical role for MyD88-mediated neutrophil recruitment during Clostridium difficile colitis." Infection and immunity 80.9 (2012): 2989-2996.

Buonomo, Erica L., and William A. Petri Jr. "The microbiota and immune response during Clostridium difficile infection." Anaerobe 41 (2016): 79-84.

Smythies LE, Maheshwari A, Clements R, Eckhoff D, Novak L, Vu HL, Mosteller-Barnum LM, Sellers M, Smith PD. Mucosal IL-8 and TGF-beta recruit blood monocytes: evidence for cross-talk between the lamina propria slioma and myeloid cells. J Leukoc Biol. Sep. 2006;80(3):492-9. doi: 10.1189/jlb.1005566. Epub Jul. 20, 2006. PMID: 16793909.

Shi, Chao, and Eric G. Pamer. "Monocyte recruitment during infection and inflammation." Nature reviews immunology 11.11 (2011): 762-774.

Perner, A., et al. "Constitutive expression of inducible nitric oxide synthase in the normal human colonic epithelium." Scandinavian journal of gaslioenterology 37.8 (2002): 944-948.

Rath, Meera, et al. "Metabolism via arginase or nitric oxide synthase: two competing arginine pathways in macrophages." Frontiers in immunology 5 (2014): 532.

Pils, Marina C., et al. "Commensal gut flora reduces susceptibility to experimentally induced colitis via T-cell-derived interleukin-10." Inflammatory bowel diseases 17.10 (2011): 2038-2046.

Miquel, Sylvie, et al. "Identification of metabolic signatures linked to anti-inflammatory effects of Faecalibacterium prausnitzii." MBio 6.2 (2015).

\* cited by examiner

TREATMENT AND PREVENTION OF PATHOGENIC BACTERIAL OVERGROWTH USING BUTYRATE-PRODUCING BACTERIA

CROSS-REFERENCE TO RELATED APPLICATIONS

This application claims priority to U.S. Provisional Application Ser. No. 62/615,124, filed on Jan. 9, 2018, which is hereby incorporated by reference in its entirety.

GOVERNMENT FUNDING

100011 This invention was made with government support under AA023266 awarded by the National Institutes of Health. The government has certain rights in the invention.

BACKGROUND

*Clostridium difficile* infection (CDI) is debilitating to patients and extremely costly, with symptoms ranging from diarrhea to fulminant colitis, toxic megacolon and death. In the United States CDI is increasing, linked to 14,000 deaths annually. CDI risk factors include antibiotic therapy; hospitalization; gastrointestinal procedures and surgery; and advanced age. Ironically, as antibiotic exposure is a major risk factor for CDI, treatment involves further antibiotic therapy. To date, the best preventative measure for CDI is restricting inappropriate antibiotic usage.

Bacteroidetes and Firmicutes are the two most abundant bacterial phyla in adults. Lopetuso et al., Gut Pathogens 5:23 (2013) Firmicutes phyla contain lactic acid and butyrate-producing bacteria (*Clostridium* clusters XIVa and IV). Types and proportions of bacteria vary within the gut, likely regulated by intestinal microenvironment and motility. Hooper et al., Annu Rev Nutr 2002; 22:283-307 (2002) Gut microbiota provide colonization resistance to pathogenic bacteria. Backhed et al., Science, 307:1915-1920 (2005) Antibiotics alter colonization resistance likely by disturbing ecologic, metabolic, and immunologic functions of the gut microbiota/host ecosystem which creates a niche that favors CD germination and growth. Theriot et al., Nat Commun, 5:3114 (2014) Characterization in global changes in microbial community structure associated with CDI and *C. difficile* (CD)-negative nosocomial diarrhea find depletion in Firmicutes phyla abundance and diversity compared to healthy microbiota. Antharam et al., J Clin Microbiology, 51:2884-2892 (2013). Of note, butyrate-producing members of the Clostridia class were significantly depleted in CDI and CD-negative mouse microbiota, but *Enterococcus* and *Lactobacillus* were unusually abundant. Additionally, corresponding with depleted butyrate-producing bacteria, mice highly contagious with CDI also had altered short-chain fatty acid (SCFA) profiles characterized by a proportional reduction in butyrate and acetate and an increase in formate, lactate, succinate levels. Lawley et al., PLoS Pathog, 8:e1002995 (2012) Increased succinate and lactate correlated with an increase in succinate and lactate-producing bacteria, respectively.

Prebiotics are indigestible carbohydrates, which upon fermentation beneficially alter gut microbiota composition as well as produce substrate specific amounts of SCFA acetate, propionate and butyrate. Pryde et al., FEMS Microbiol Lett, 217:133-139 (2002). Of various carbohydrate tested, resistant starch yields a higher molar ratio of butyrate compared to other prebiotics. Cummings et al., Am J Clin Nutr, 73:415s-420s (2002) Although the least abundant SCFA in the colonic lumen, butyrate is the most dynamic. Butyrate induces epithelial cell proliferation in normal intestinal tissue, but decreases cell proliferation and increases apoptosis in colon cancer cells, stimulates electrolyte and water absorption, is the primary fuel source for colonocytes and improves gut barrier function, and is anti-inflammatory and immunomodulatory through inhibition of transcription factor NF-kB. Inan et al., Gastroenterology, 118:724-734 (2000) Absence of butyrate in intestinal tissue is associated with inflammation and mucosal atrophy. Thangaraju et al., Cancer Research, 69:2826-32 (2009)

Probiotics are beneficial bacteria which, when consumed in adequate amounts, positively affect the host. Hill et al., Nat Rev Gastroenterol Hepatol, 11:506-514 (2014). While not fully elucidated, probiotics are proposed to compete with pathogenic microbes for available nutrients and epithelial binding sites, decrease luminal pH making it less favorable for pathogenic bacteria, modulate the immune response, and reestablish intestinal barrier function. Probiotic effects are strain specific, making the choice of probiotic crucial for therapeutic success. Various strains and combinations of probiotics have been attempted, with variable effects, to treat and prevent antibiotic-associated and CD-associated diarrhea with *Lactobacillus* species most commonly tested.

*Faecalibacterium prausnitzii* is an anaerobic commensal butyrate-producing bacterium and a dominant member of the *Clostridium leptum* subgroup known to have anti-inflammatory properties. Miguel et al., Curr Opin Microbiol, 16:255-61 (2014) FP is widely distributed in the intestine and accounts for approximately 5% of total fecal microbiota in healthy adults. Many diseases are associated with depleted levels of FP, including CDI.

SUMMARY OF THE INVENTION

As antibiotics provoke gut dysbiosis and CD induces diarrhea, intestinal inflammation and potential mucosal injury, the aim inventors investigated the effects of oral supplementation with a butyrate-producing bacteria (FP) and butyrate-yielding prebiotic (PS) on bacterial colonization and colonic health in mice treated with antibiotics and exposed to CD.

*Clostridium difficile* is a significant healthcare-associated pathogen with rising infection rates in US hospitals and long-term care facilities. Gut microbiota are known to markedly influence host biology. Depleting gut microbiota and its beneficial metabolic and fermentation byproducts, antibiotics are both a risk factor and treatment for CD infection. With a need to alleviate consequences linked with commensal gut microbial perturbations caused by antibiotics and subsequent CD infection, the inventors supplemented a commensal anti-inflammatory butyrate-supporting bacteria and prebiotic during antibiotic and CD exposure and found effective innate immune responses, enhanced resolution of bacterial overgrowth, and protection of gut integrity in supplemented mice. These results show that supplementation with a commensal anti-inflammatory butyrate-supporting bacteria and prebiotic during antibiotic therapy may offer therapeutic benefit to preserving innate immune responses necessary to combat CD pathogenicity.

BRIEF DESCRIPTION OF THE FIGURES

The present invention may be more readily understood by reference to the following figures, wherein:

FIGS. 1A and 1B provide graphs showing the effect of antibiotic treatment on bacterial overgrowth. Mice were randomized into groups and supplemented daily with FP, PS, FP+PS, supernatant, or saline. Mice were treated with daily subcutaneous injections of saline or clindamycin (1.4 mg/d) for 3 days. Following transfer to clean cages, fresh feces were collected and concentration of *enterococcus* and gram-negative bacteria was measured by plating serially diluted samples on selective agar at A) Baseline prior to antibiotics and B) 1 day following last dose of antibiotic. Data are presented as mean $\log_{10}$ CFU/gm±SEM and percentage of animals in each group with range of $\log_{10}$ CFU/gm set as none, 1-3, 4-5, 6-7, 8-9, >9 $\log_{10}$ CFU/gm. n=12-13 animals/group.

FIGS. 2A-2C provide graphs showing the bacterial colonization following CD exposure. Mice were randomized into groups and treated with saline or clindamycin as described in FIG. 1. Three days following the last dose of clindamycin, mice were orally exposed to VA17 (4-$\log_{in}$ CFU/mL). Mice received the randomized supplements daily. Concentration of *enterococcus*, gram negative bacteria and CD was measured by plating serially diluted fresh stool samples on selective agar on A) day 1 B) day 3 and C) day 5 after CD challenge. Data are presented as mean $\log_{10}$ CFU/gm±SEM and percentage of animals in each group with range of $\log_{10}$ CFU/gm set as none, 1-3, 4-5, 6-7, 8-9, >9 $\log_{10}$ CFU/gm. n=10 animals/group.

FIGS. 3A-3C provide graphs showing the effect of *F. prausnitzii* and potato starch on bacterial colonization recovery. Mice received supplementation with FP+PS or saline and received clindamycin and CD as described in FIGS. 1 and 2. Fresh stool was cultured on selective agar for concentration of *enterococcus*, gram negative bacteria and CD measured by plating serially diluted samples on A) day 1 B) day 3 and C) day 5 after CD challenge. Data are presented as mean $\log_{10}$ CFU/gm±SEM. Values with different alphabetical superscripts were significantly different from each other, $p<0.05$.

FIGS. 5A and 5B provide a graph and images showing a comparison of *F. prausnitzii* plus potato starch with saline on butyrate transporter and pathogen receptors. Mice were treated as described in FIGS. 1 and 2. Proximal colon was collected and used to prepare RNA or embedded in OCT for histology on day 1 and 5 following CD exposure. A) Expression of TLR2 mRNA was detected in proximal colon of mice using quantitative real-time reverse transcription polymerase chain reaction. Data are the mean fold change ±SEM. * $p<0.05$. B) SLC5A8 (green) and C) FZD7 (green) were visualized by immunohistochemistry in sections of proximal colon frozen in OCT. All images were acquired using a 40× objective. Images are representative of at least replicate images captured per mouse in 6 mice per treatment group at time point 5 days following CD exposure.

FIGS. 6A-6F provide graphs showing the effect of *F. prausnitzii* plus potato starch on chemokine and cytokines following CD exposure. Mice were treated as described in FIGS. 1 and 2. Proximal colon was collected and used to prepare RNA. A-F) Expression IL1β, MCP1, IL8, ELANE, IL10, and iNOS mRNA were detected in proximal colon of mice using quantitative real-time reverse transcription polymerase chain reaction. Data are the mean fold change ±SEM. Values with * and different alphabetical superscripts were significantly different from each other, $p<0.05$.

DETAILED DESCRIPTION OF THE INVENTION

The present invention provides a method of treating or preventing overgrowth by pathogenic bacteria in a subject deficient in butyrate and/or butyrate-producing bacteria in their gut microbiota by administering a therapeutically effective amount of a butyrate-producing bacteria to the subject.

Definitions

As used herein, the terms "treatment," "treating," and the like, refer to obtaining a desired pharmacologic or physiologic effect. The effect may be therapeutic in terms of a partial or complete cure for a disease or disorder such as overgrowth by pathogenic bacteria, or an adverse effect attributable to the disease or disorder. "Treatment," as used herein, covers any treatment of a disease or disorder in a mammal, particularly in a human, and can include inhibiting the disease or condition, i.e., arresting its development; and relieving the disease, i.e., causing regression of the disease.

As used herein, the term "prevention" includes either preventing or decreasing the likelihood or severity of the onset of overgrowth by pathogenic bacteria altogether or preventing or decreasing the likelihood or severity of the onset of a preclinical overgrowth by pathogenic bacteria in individuals at risk. This includes prophylactic treatment of those having an enhanced risk of developing an overgrowth of pathogenic bacteria. An elevated risk represents an above-average risk that a subject will develop overgrowth by pathogenic bacteria, which can be determined, for example, through family history, detection of genes causing a predisposition to developing overgrowth by pathogenic bacteria, or treatment with antibiotics.

The terms "microbiota", "microflora" and "microbiome" preferably mean a community of living microorganisms that typically inhabits a bodily organ or part.

The terms "therapeutically effective" and "pharmacologically effective" are intended to qualify the amount of an agent which will achieve the goal of improvement in disease severity and the frequency of incidence over treatment of each agent by itself, while avoiding adverse side effects typically associated with alternative therapies. The effectiveness of treatment may be measured by evaluating a reduction in symptoms or prevention/resolution of bacterial overgrowth, bacterial infection, or pathology.

"Assessing the risk of a subject developing a disease or condition" refers to the determination of the chance or the likelihood that the subject will develop the disease or condition. This may be expressed as a numerical probability in some embodiments. The assessment of risk may be by virtue of the extent of dysbiosis determined by the methods of the invention.

The terms "subject" and "patient" can be used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets, veterinary animals, and animals maintained in zoos. Treatment and evaluation of human subjects is of particular interest. Human subjects can be various ages, such as a child (under 18 years), adult (18 to 59 years) or elderly (60 years or older) human subject.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "about" refers to +/−10% deviation from the basic value.

Unless defined otherwise, all technical and scientific terms used herein have the same meaning as commonly understood by one of ordinary skill in the art to which this invention belongs.

Treating or Preventing Overgrowth by Pathogenic Bacteria

The present invention provides a method of treating or preventing overgrowth by pathogenic bacteria in a subject deficient in butyrate and/or butyrate-producing bacteria in their gut microbiota by administering a therapeutically effective amount of a butyrate-producing bacteria and/or a prebiotic to the subject. The "gut," as defined herein, refers to the gastrointestinal tract, and any portion thereof. Parts of the gastrointestinal tract include the stomach, colon, small intestine, rectum, anus, and mouth. In some embodiments, overgrowth by pathogenic bacteria prevented, or the risk of developing overgrowth by pathogenic bacteria is decreased. In particular, the risk of overgrowth by pathogenic bacteria can be decreased in individuals identified as being at risk of developing pathogenic bacterial overgrowth. In other embodiments, a subject deficient in butyrate and/or butyrate-producing bacteria is treated to decrease or eliminate overgrowth by pathogenic bacteria.

Bacterial overgrowth is a condition in which the normal gastrointestinal bacterial flora is overtaken by proliferation of pathogenic bacteria. Bacterial overgrowth can include about a 10%, 20%, 30%, 40%, 50%. 60%, 70%, 80%, 90%, 100%, 150%, 200%, 300%, or more than 300% increase in pathogenic bacteria. It frequently occurs in patients in a weakened state of health, such as patients with compromised immunity, including transplant patients, AIDS patients, scleroderma patients, cancer, etc. The condition is usually marked by bloating, diarrhea and/or constipation, liquid stools, uncontrollable belching, and/or esophageal refluxing. S. A. Kaye et al., British Journal of Rheumatology, Vol. 34, p. 265 (1995) describes the condition of small bowel bacterial overgrowth in systemic sclerosis. In some cases the overgrowth is due to a specific bacterium, such as a *C. difficile*, in other cases it may be due to a mixture of bacterial species and other organisms such as yeast, parasitic pathogens or viral pathogens.

As used herein "pathogenic bacteria" refer to bacteria capable of causing an infection in the gastrointestinal tract of a subject, including a human. Examples of pathogenic bacteria include, but are not limited to *Aeromonas hydrophilia*, *Bacillus cereus*, *Vibrio parahemolyticus*, *Vibrio cholerae* 01, *Vibrio cholera* non-01, *Vibrio vulnificus*, *Salmonella enteric*, *Salmonella typhi*, *Salmonella paratyphi*, *Salmonella entertidis*, *Salmonella cholerasuis*, *Salmonella typhimurium*, *Clostridium difficile*, *Clostridium botulinum*, *Clostridium perfringens*, *Staphylococcus aureus*, *Escherichia coli* (—various subclasses), *Campylobacter jejuni*, *Campylobacter coli*, *Campylobacter lari*, *Campylobacter fetus*, *Yersinia enterocolitica*, *Yersinia pestis*, *Yersinia pseudotuberculosis*, *Plesiomonas shigelloides*, and *Listeria monocytogenes*. In some embodiments, the pathogenic bacteria is *Clostridium difficile*.

In some embodiments, the overgrowth by pathogenic bacteria is caused by antibiotic administration to the subject. Antibiotic administration can disrupt the normal gut microbiota, allowing overgrowth by pathogenic bacteria to occur. Antibiotic administration includes administration of a single antibiotic, or a plurality of antibiotics. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephetns (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefdi toren, cefoperazone, cefotaxirne, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levoiloxacin, lomefloxacin, moxifloxacin, norfloxacin, ofloxacin, trovafloxacin), rifamycins rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. Particularly disruptive are broad-spectrum antibiotics such as fluoroquinolones.

The present invention provides a method of treating or preventing overgrowth by pathogenic bacteria in a subject by administering a therapeutically effective amount of a butyrate-producing bacteria to the subject. Butyrate-producing bacteria have the capacity to break down various resistant starches for their metabolism, thereby producing butyrate and other short-chain fatty acids. Butyrate-producing bacteria can be readily identified using methods known to those skilled in the art. Louis P, Flint H J, FEMS Microbiol Lett. 294, 1-8 (2009). A large number of butyrate-producing bacteria are found in the families Ruminococcaceae, Eubacteriaceae, Lachnospiraceae, and Clostridiales. Examples of butyrate-producing bacterial species include *Faecalibacterium prausnitzii*, *Eubacterium rectale*, *Roseburia faecis*, *Roseburia inulinivorans*, *Roseburia intestinalis*, *Eubacterium halii*, *Anarostipes caccae*, *Coprococcus comes*, *Subdoligranulym variabile*, *Coprococcus catus*, *Roseburia hominis*, *Coprococcus eutactus*, *Anaerotruncus*

*colihominis*, *Eubacterium cylindroids*, and *Butyrivibria fibrisolvens*. See Pryde et al., FEMS Microbiol. Lett. 217, 133-139 (2002) and Dillon et al., AIDS, 31(4), 511-521 (2017), the disclosures of which are incorporated herein by reference. A preferred butyrate-producing bacteria for use in the methods described herein is *Faecalibacterium prausnitzii*.

Treatment or prevention of overgrowth by pathogenic bacteria should be carried out only in subjects who have been identified as being at risk of developing, or currently manifesting a disturbance of their gut microbiota. In some embodiments, the subject has been identified as being a subject deficient in butyrate and/or butyrate-producing bacteria in their gut microbiota. Symptoms of disturbance of gut microbiota are known to those skilled in the art, and the composition of the gut microbiota can be readily identified using cell culturing and/or 16S rRNA sequencing. Dillon et al., Mucosal Immunol. 7, 983-994 (2014).

In some embodiments, the subject is identified as being deficient in butyrate-producing bacteria. Butyrate-producing bacteria have already been described herein. In some embodiments, the subject is deficient in the butyrate-producing bacteria *Faecalibacterium prausnitzii*. A subject is deficient in butyrate-producing bacteria if the subject has a lower than normal level of the bacteria in their gut microbiota. This can be determined by comparing the current level of butyrate-producing bacteria to the level found in a typical healthy subject, or by comparing the current level of butyrate-producing bacteria to an earlier determination of the level of butyrate-producing bacteria from the subject at a time when they were known to be healthy with regard to their gut microbiota. A deficient subject can have a 10%, 20%, 30%, 40%, 50%, 60%, 70%, 80%, 90%, or 100% decrease in their level of butyrate-producing bacteria in comparison with a healthy subject.

Alternately, or in addition, the subject being treated can be one who has been shown to be deficient in butyrate in their gut. Butyrate, or butanoate, is the conjugate base of butyric acid, which has the formula $C_4H_8O_2$. Butyrate, as used herein includes both the conjugate base and acid forms. Butyrate deficiency would typically be due to a deficiency in butyrate-producing bacteria. A subject is deficient in butyrate if the subject has a lower than normal level of the butyrate in their gut. This can be determined by comparing the current level of butyrate to the level found in a typical healthy subject, or by comparing the current level of butyrate to an earlier determination of the level of butyrate from the subject at a time when they were known to be healthy with regard to their gut microbiota. A deficient subject can have a 10%, 20%, 30%, 40%, 50%, 60%, 70%, 80%, 90%, or 100% decrease in their level of butyrate in comparison with a healthy subject.

After an appropriate period of time (e.g., after an initial period of treatment) from the administration of the butyrate-producing bacteria, e.g., 5-30 days, the level of bacterial overgrowth is determined again. In some embodiments, the level of bacterial overgrowth is determined periodically throughout treatment. For example, the bacterial overgrowth can be checked every few days or weeks to assess the further efficacy of the treatment. A decrease in bacterial overgrowth indicates that the treatment is efficacious. Efficacy of a treatment can be measured as reduction of bacterial overgrowth, or can be measured in terms of a reduction of symptoms associated with a gut-related disorder, a stabilization of symptoms, or a cessation of symptoms associated with a gut-related disorder.

Bacterial Compositions

The composition of the invention comprises butyrate-producing bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilized bacteria. Lyophilization of bacteria is a well-established procedure and relevant guidance is available. Miyamoto-Shinohara et al., J. Gen. Appl. Microbiol., 54, 9-24 (2008). Alternatively, the composition of the invention may comprise a live, active bacterial culture.

Typically, a nutritional carrier is co-administered with the butyrate-producing bacteria to the subject. A nutritional carrier is a material included with the bacteria that provides nutrients for the bacteria. In some embodiments, the nutritional carrier is a prebiotic. A prebiotic compound is usually a non-digestible carbohydrate such as an oligo- or polysaccharide, or a sugar alcohol, which is not degraded or absorbed in the upper digestive tract. Upon fermentation, prebiotics produce short-chain fatty acids such as butyrate. In some embodiments, the prebiotic is starch, such as a resistant starch. The starch can be obtained from any suitable source, such as potato starch. Known prebiotics include commercial products such as inulin and transgalacto-oligosaccharides.

In certain embodiments, the composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference Handbook of Pharmaceutical Excipients, 2nd Edition, (1994), Edited by A Wade and P J Weller. Acceptable carriers or diluents for therapeutic use are well known in the pharmaceutical art and are described, for example, in reference Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilizing agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated with a nutritious product such as a juice, fermented beverage, or milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavored milks, ice cream; milk-containing food such as sweets. Examples of fermented beverages include kombucha, beer, wine, and kefir.

In some embodiments in which the composition of the invention comprises more than one bacterial strain, species or genus, the individual bacterial strains, species or genera may be used for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strain, species or genera are stored separately but are mixed together prior to use.

In some embodiments, the compositions of the invention comprise one or more bacterial strains of the species *Faecalibacterium prausnitzii* and do not contain bacteria from any other genus, or which comprise only de minimis or biologically irrelevant amounts of bacteria from another genus. Thus, in some embodiments, the invention provides a composition comprising one or more bacterial strains of the species *Faecalibacterium prausnitzii*, which does not contain bacteria from any other genus or which comprises only de minimis or biologically irrelevant amounts of bacteria from another genus, for use in therapy.

Administration

Preferably, the compositions of the invention are administered to the gastrointestinal tract in order to enable delivery to and/or partial or total colonization of the intestine with the bacterial strain of the invention. Generally, the butyrate-producing bacteria are administered orally, but they may be administered rectally, intranasally, or via buccal or sublingual routes.

In some embodiments, the composition of the invention (e.g., the butyrate-producing bacteria) is administered in a pharmaceutically acceptable carrier. For example, the compositions of the invention may be administered as a foam, as a spray or a gel. In certain embodiments, the compositions of the invention may be administered as a suppository, such as a rectal suppository, for example in the form of a *theobroma* oil (cocoa butter), synthetic hard fat (e.g. suppocire, witepsol), glycero-gelatin, polyethylene glycol, or soap glycerin composition.

In some embodiments, the pharmaceutically acceptable carrier is a capsule. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, Mitropoulou et al. J Nutr Metab. 2013, 716861 (2013).

The composition may be administered orally and may be in the form of a tablet, capsule or powder. Other ingredients (such as vitamin C, vitamin A and its derivatives, for example), may be included as oxygen scavengers or immune modulators and prebiotic substrates to improve the delivery and/or partial or total colonization and survival in vivo. Alternatively, the composition of the invention may be administered orally as a food or nutritional product, such as milk or whey based fermented dairy product, or as a pharmaceutical product. In some embodiments, the compositions of the invention may be administered together with a prebiotic.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In some embodiments, the butyrate-producing bacteria are administered to the subject a plurality of times over a week or more of time. In certain embodiments, the compositions of the invention are to be administered daily.

In certain embodiments of the invention, treatment according to the invention is accompanied by assessment of the subject's gut microbiota. Treatment may be repeated if delivery of and/or partial or total colonization with the strain of the invention is not achieved such that efficacy is not observed, or treatment may be ceased if delivery and/or partial or total colonization is successful and efficacy is observed.

The compositions of the invention may be administered to a subject that has been identified as having an abnormal gut microbiota. For example, the subject may have reduced or absent colonization by *Faecalibacterium prausnitzii*.

For reducing bacterial overgrowth, the amount of butyrate-producing bacteria required to be administered to the subject will vary depending upon factors such as the risk and severity of the bacterial overgrowth, the age of the subject, the form of the composition, and other medications being administered to the subject. A suitable daily dose of the bacteria, for example for an adult human, may be from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g of the composition.

An example has been included to more clearly describe particular embodiments of the invention. However, there are a wide variety of other embodiments within the scope of the present invention, which should not be limited to the particular example provided herein.

EXAMPLE

Example 1: *Faecalibacterium prausnitzii* and a Probiotic Protect Intestinal Health During Antibiotic and *Clostridium difficile* Exposure

*Clostridium difficile* infection (CDI) causes increased patient morbidity, mortality and health care costs. Antibiotic treatment induces gut dysbiosis, and is both a major risk factor for CD colonization and treatment of CDI. Probiotics have been trialed to support commensal gut microbiota and reduce CDI. This study investigated commensal microbe *Faecalibacterium prausnitzii* (FP) and a prebiotic, both known to yield butyrate and be anti-inflammatory and immunomodulatory, on CD colonization and gut integrity in mice.

Materials and Methods

Reagents:

Sodium butyrate, potato starch (Sigma-Aldrich; St. Louis, Mo.). All primers for quantitative real-time reverse transcription polymerase chain reaction (qRT-PCR) were synthesized by Integrated DNA Technologies (Coralville, Iowa, USA). Antibodies were purchased from the following sources: anti-sodium hydrogen exchanger 3 (NHE3), anti-zona occludin-1 (ZO-1), anti-Sodium-coupled monocarboxylate transporter 1 SLC5A8), and anti-frizzled class receptor 7 (FZD-7) from Abcam (Cambridge, Mass.); anti-occludin from Hycult Biotechnologies (Plymouth meetings, PA); anti-claudin-3, Alexa fluor 488 and 568 IgG from Invitrogen (Camarillo, Calif.).

*Clostridium difficile* Strain:

VA17 is an epidemic North American pulsed-field gel electrophoresis type 1 (NAP1) CD strain. CD spores were prepared as previously described, and animals were treated with 4 $\log_{10}$ colony-forming units (CFU) in 10 µL of phosphate-buffered saline (PBS). US Environmental Protection Agency Office of Pesticide Programs, Standard Operating Procedure for Production of Spores of *Clostridium difficile* for Use in the Efficacy Evaluation of Antimicrobial Agents, SOP Number: MB-28-04, Office of Pesticide Programs, Microbiology Laboratory, Environmental Science Center, Ft. Meade, Md., Jun. 19, 2014.

Treatment Design:

Treatment included butyrate-producing bacteria (*Faecalibacterium prausnitzii* (FP), ATCC 27766) (Duncan et al., Internat J System Evolutionary Microbiology, 52:2141-2146 (2002)) 6 $\log_{10}$ CFU/10 µL and potato starch (PS) (20% w/v). This strain was chosen because it was isolated from human feces, and based on its ability to hydrolyze PS, yield butyrate, and utilize lactate. Belenguer et al., Applied Environmental Microbiology, 72:3593-3599 (2006) Bacteria was grown in conditions and medium as recommended by ATCC, briefly at 37° C. in anaerobic gas biological mix of 80% nitrogen, 10% carbon dioxide, 10% hydrogen, ATCC pre-reduced chopped meat broth (ATCC 1703). Overnight culture of FP was lyophilized on savant system and reconstituted in pre-reduced sterile phosphate buffered saline (PBS) just prior to treatment.

Minimum Inhibitory Concentration (MIC):

*Brucella* broth dilution MIC of common antibiotics for FP and CD strains were determined using standard methods for susceptibility testing of anaerobic bacteria (Table 1).

TABLE 1

MICs against common antibiotics for *F. prausnitzii* and *C. difficile* strains used in this study

|  | *F. prausnitzii* MIC | *C. difficile* MIC |
| --- | --- | --- |
| Cefoxitin | <2 | 250 |
| Clindamycin | <2 | 500 |
| Piperacillin/Tazaba | 8 | 15.63 |
| Vancomycin | <2 | <2 |
| Metronidazole | <2 | <2 |
| Positive control | Positive | Positive |
| Negative control | Negative | Negative |

In Vivo Mouse Model of CD Colonization Resistance and Bacterial Overgrowth:

A previously described mouse model evaluating recovery of colonization resistance after antibacterial treatment was used. Pultz N J, Donskey C J., Antimicrob Agents Chemother, 49:3529-3532 (2005) Female CF-1 mice (Harlan Sprague-Dawley, Inc/ENVIGO, Indianapolis, Ind.) weighing 25-30 gm were housed individually in micro-isolator cages and fed sterilized Teklad Global 18% Protein extruded rodent diet (Harlan Teklad, Madison, Wis.). Mice received daily subcutaneous injections (0.1 mL total volume) of saline (control) or clindamycin (1.4 mg/d) for 3 days. The dose of antibiotic was equal to the usual human dose administered over 24-h period. Three days later, mice were orally exposed to VA17 (4-$\log_{10}$ CFU/10 µL). Throughout the treatment period, mice (10-13 per group) were randomized to receive orally one of the following treatments daily: saline (control), *Faecalibacterium prausnitzii* (FP), potato starch (PS), FP+PS, or supernatant from FP+PS culture. Fresh stool specimens were collected on days 1, 3 and 5 after CD challenge and concentration of *enterococcus*, gram negative bacteria and CD was measured by plating serially diluted samples on selective agar as previously described. Pultz, Ibid. Colonization resistance was deemed intact in clindamycin-treated mice receiving FP and/or PS if there was no significant increase in concentrations of CD in stool in comparison to saline controls. On day 1 and 5, mice were randomly chosen from each treatment group and euthanized by $CO_2$ asphyxiation and proximal colon was dissected and frozen in optimal cutting temperature medium (OCT) (Sakura Finetek USA, Torrance, Calif.) or stored in RNAlater (Ambion, Austin, Tex.) for further analysis. Proximal colon was analyzed as this is a main location of CD pathogenicity.

Immunohistochemistry:

Frozen sections of proximal colon embedded in optimal cutting temperature solution (OCT) were mounted on glass slides that were coded before analysis. Slides were air dried and fixed with 4% paraformaldehyde, washed with 1X phosphate-buffered saline (PBS). Sections were blocked with 2% bovine serum albumin (dissolved in 1×PBS) containing 0.1% TRITON-X-100, then blocked again with 2% BSA only. Slides were incubated with primary antibodies overnight at 4° C., washed with 1×PBS, incubated with secondary antibodies, then washed with 1×PBS, and mounted with DAPI-containing mounting media (VECTASHIELD #H-1200, Vector laboratories, Burlingame, Calif., USA). Fluorescent images were acquired using a LEICA confocal microscope with 3 images captured per slide.

Quantitative Real-Time Reverse Transcription Polymerase Chain Reaction.

Total RNA was isolated from proximal colon from at least 3-10 mice per experimental condition, and 2 ug of total RNA was reverse transcribed using the RETRO SCRIPT kit (Invitrogen Ambion, Vilnius, Lithuania) with random decamers as primer. Briefly, to melt RNA secondary structure the RNA and random decamer were incubated at 80° C. for 3 minutes, cooled to 42°, then remaining reaction mixture components were added. During a 60-minute incubation at 42° C. first-strand synthesis was performed, followed by a 10-minute incubation at 92° C. to inactivate the Moloney Murine Leukemia virus (MMLV)-reverse transcriptase enzyme. Real-time PCR amplification was performed using POWER SYBR qRT-PCR kits (Applied Biosystems, Foster City, Calif.) on QuantStudio 5 analyzer (Applied Biosystems Foster City, Calif.) for primers: monochemoattractant protein-1 (MCP1), neutrophil elastase (ELANE), interleukin-8 (IL8), IL1β, IL10, toll-like receptor-2 (TLR2), inducible nitric oxide synthase (iNOS), glyceraldehyde 3-phosphate dehydrogenase (GAPDH), and 18S. Relative amount of target mRNA was determined using comparative threshold (Ct) method by normalizing target mRNA Ct values to those of 18S or GAPDH and represented as fold change relative to saline-treated mice.

Statistical Analysis

All data are expressed the mean±standard error of the mean (n=3-10 mice). Student's t-test was used for parametric analysis of two groups; analysis of variance (ANOVA) was used for comparison of multiple groups with a Tukey's post hoc test for multiple comparisons. Statistical significance was defined as $p<0.05$.

Results

Antibiotic Treatment Promoted Bacterial Overgrowth

Figure 1A:
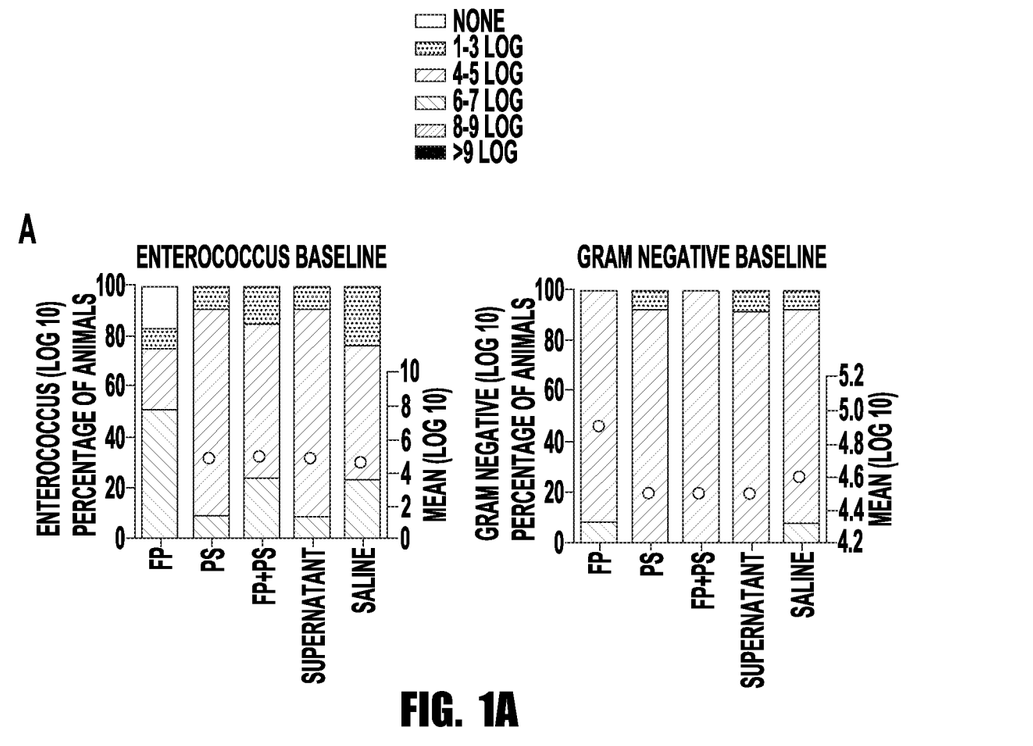
Figure 1B:
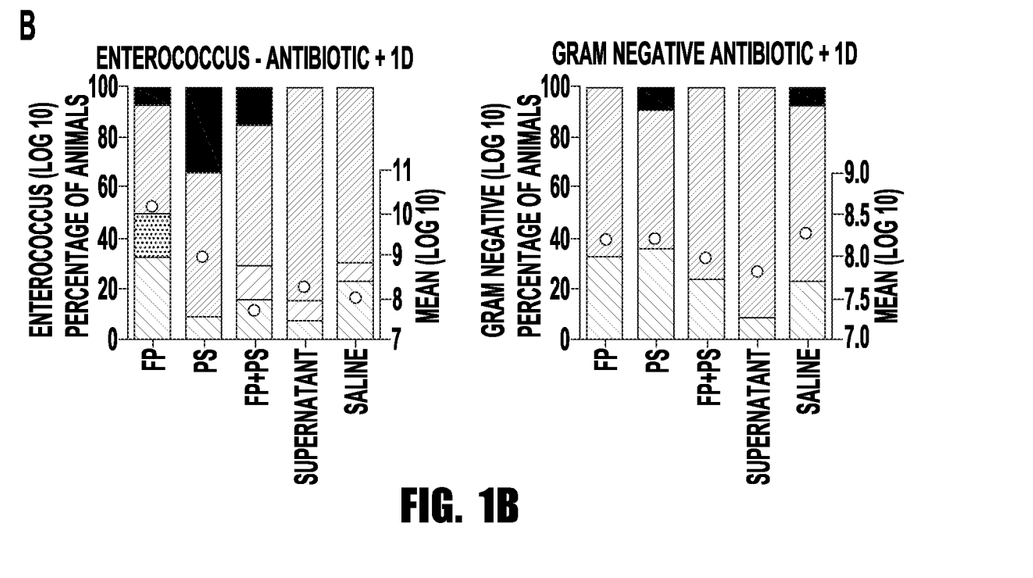

The fecal contents of mice were similar in *enterococcus* and gram-negative bacteria concentration at baseline (approximately 4 $\log_{10}$ CFU/gm) (FIG. 1A). Following 3 days of clindamycin, the mean value of both *enterococcus* and gram negative in fecal content significantly increased in all treatment groups (approximately 8 $\log_{10}$ CFU/gm) (FIG. 1B). Of note, not all animals in each group colonized equally.

Bacterial Overgrowth and *Clostridium difficile* Colonization

Figure 2A:
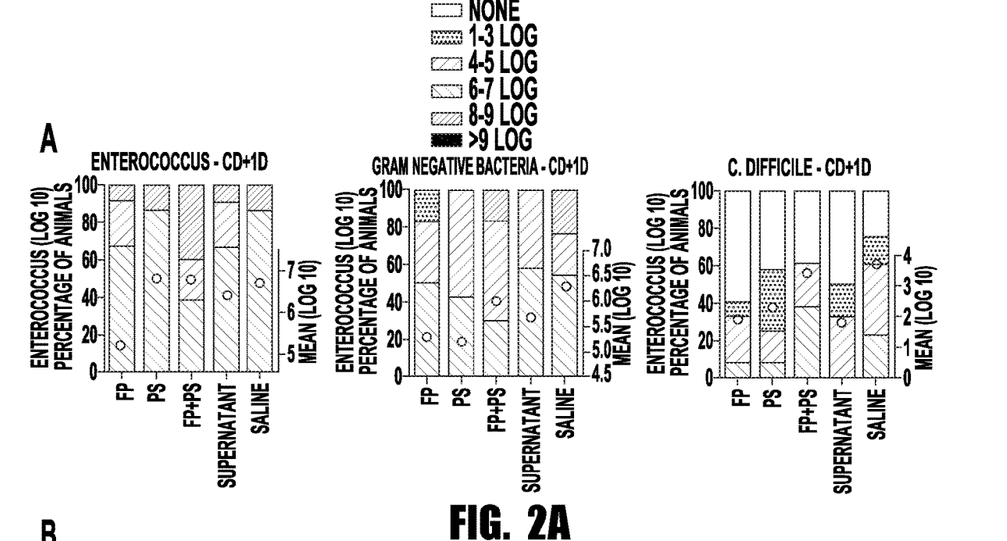
Figure 2B:
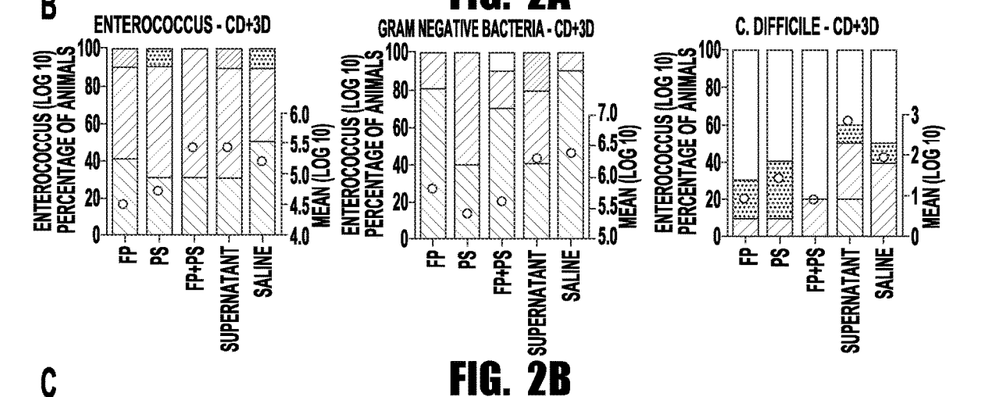
Figure 2C:
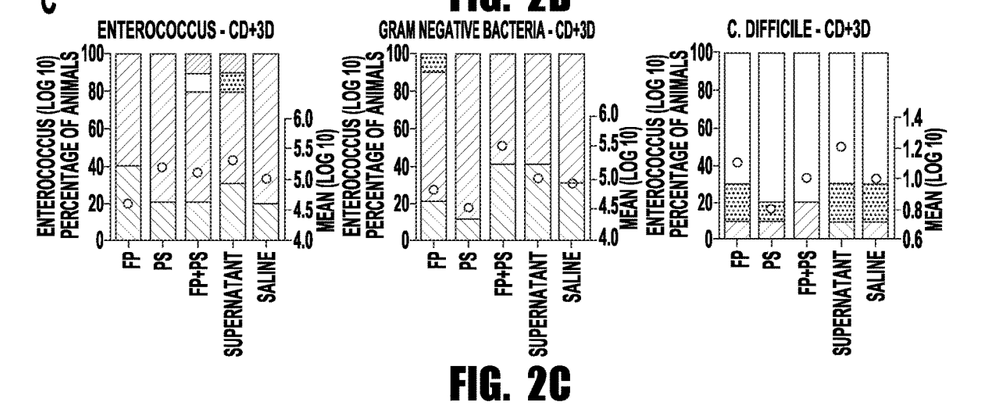
Figure 3A:
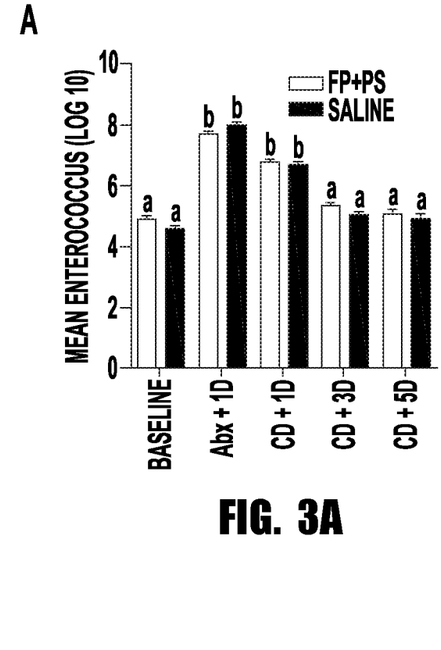
Figure 3B:
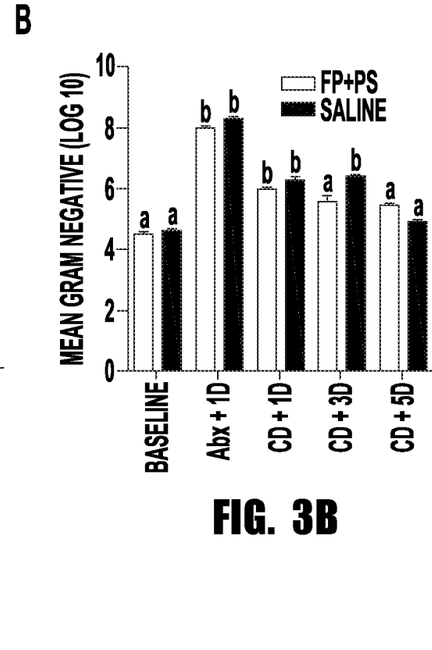
Figure 3C:
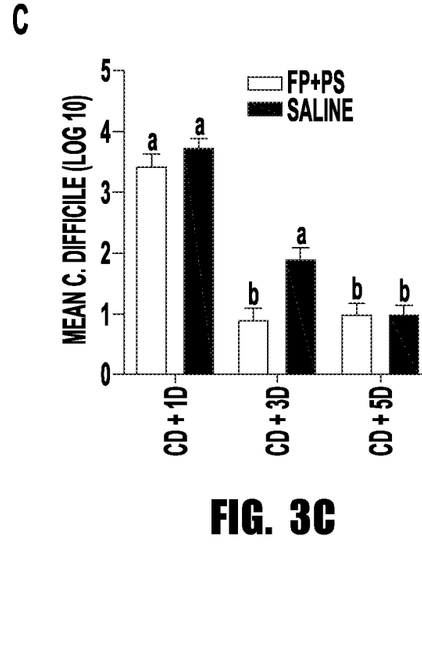

Bacterial overgrowth of *enterococcus* and gram-negative bacteria persisted throughout the study period (FIG. 2). As expected, overgrowth diminished and was to near baseline levels by 9 days following the last dose of clindamycin (approximately 5 $\log_{10}$ CFU/gm). Exposure to CD (4 $\log_{10}$ CFU) three days following the last dose of clindamycin supported fecal growth of CD where the mean CFU/gm for all treatment groups was 2.6 $\log_{10}\pm0.7$. CD colonization diminished during the study period and was to near baseline levels 5 days following exposure (1 $\log_{10}$ CFU/gm±0.6). While mean CFU/gm colonization was not statistically different between the groups at each time point, interestingly, there was variability amongst the animals within each treatment group in regards to the incidence and/or level of bacterial overgrowth and colonization (FIG. 2). Where 60% of animals in the supernatant group, 50% in saline, 40% in PS, and 30% in FP were colonized with CD three days following exposure, the FP+PS treatment group exhibited clearance of CD in all but 20% of animals (2 of 10 mice) 3 days following exposure to CD. Although clearance of *enterococcus* was similar between the FP+PS and saline animals (FIG. 3A), the FP+PS animals showed significant improvement in colonization with both gram-negative bacteria and CD 7 days following the last dose of clindamycin and 3 days following CD exposure compared to the saline treated animals (FIGS. 3B & C).

Figure 4A:
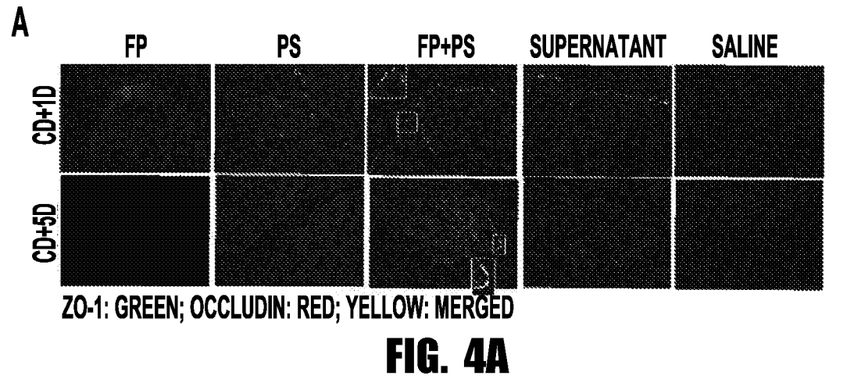
FIGS. 4A-4C provide images showing the effects of CD on tight junction protein and an anion exchanger expression in proximal colon. Mice were treated as described in FIGS. 1 and 2. Proximal colon was collected and embedded in OCT for histology on day 1 and 5 following CD exposure. A) Occludin (red), ZO-1 (green); B) claudin-3 (green); C) NHE3 (green) were visualized by immunohistochemistry in sections of proximal colon frozen in OCT. A selected area was cropped and enlarged. All images were acquired using a 40× objective. Images are representative of at least replicate images captured per mouse in 3-6 mice per treatment group.
Figure 4B:
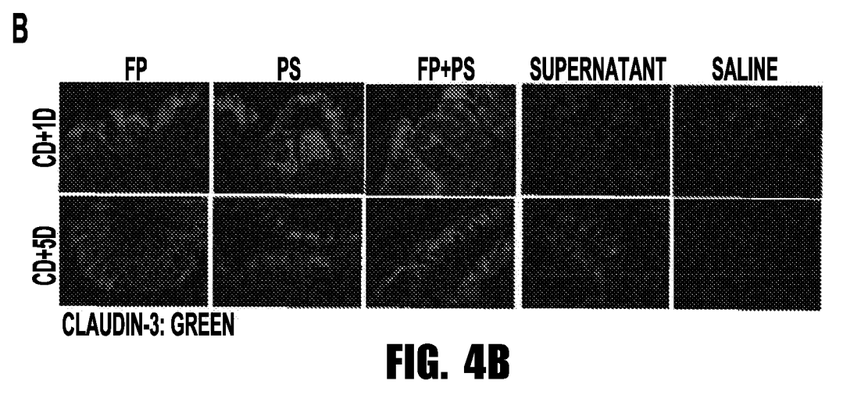
Figure 4C:
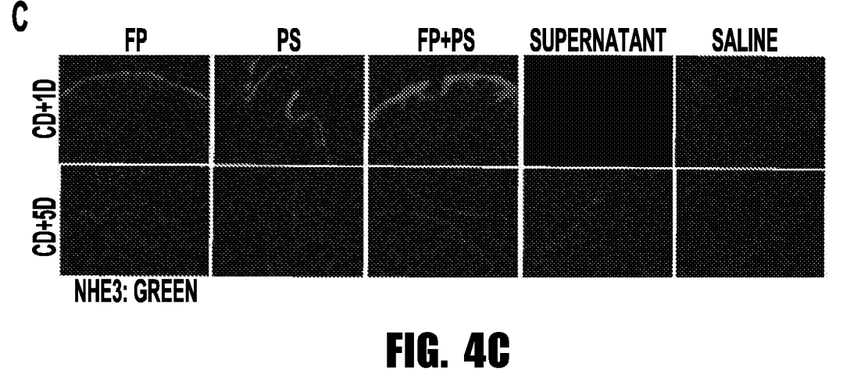

*F. prausnitzii* and potato starch mitigated CD-induced disruption of an anion exchanger and TJ proteins NHE3 is a sodium-hydrogen ion antiporter previously shown to be downregulated in germ-free mice, by antibiotic treatment and in patients with CDI. Cresci et al., J Gastrointest Surg, 14:449-461 (2010) Loss of NHE3 is associated with dissociation of intestinal tight-junction proteins. Cresci et al., J Parent Enteral Nutr, 37:763-774 (2013). To assess colonic expression of NHE3 and intestinal epithelial integrity, we assessed cell-to-cell junctional markers occludin, ZO-1, claudin-3, and NHE3 by immunofluorescence. Clindamycin treatment followed by CD exposure caused delocalization of TJ proteins (ZO-1, occludin, claudin-3) as well as the anion exchanger NHE3 in proximal colon of control mice (FIG. 4A-C). Co-supplementation with PS, FP, PS+FP and supernatant maintained immunoreactive staining intensity of NHE3 and TJ proteins and co-localization of ZO-1 and occludin, with the PS+FP appearing most robust. Protein expression visually appeared intact at both 1 and 5 days post CD exposure in the supplemented groups, however the depleted levels observed in the saline group at day 1 seemed to diminish further by day 5.

Figure 5A:
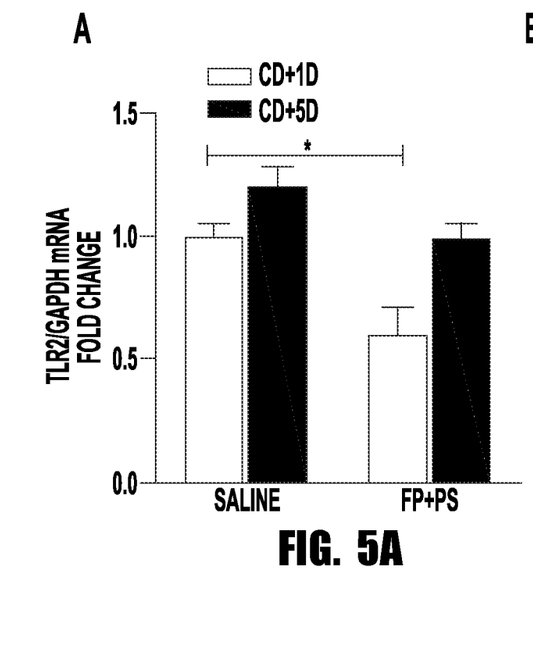
Figure 5B:
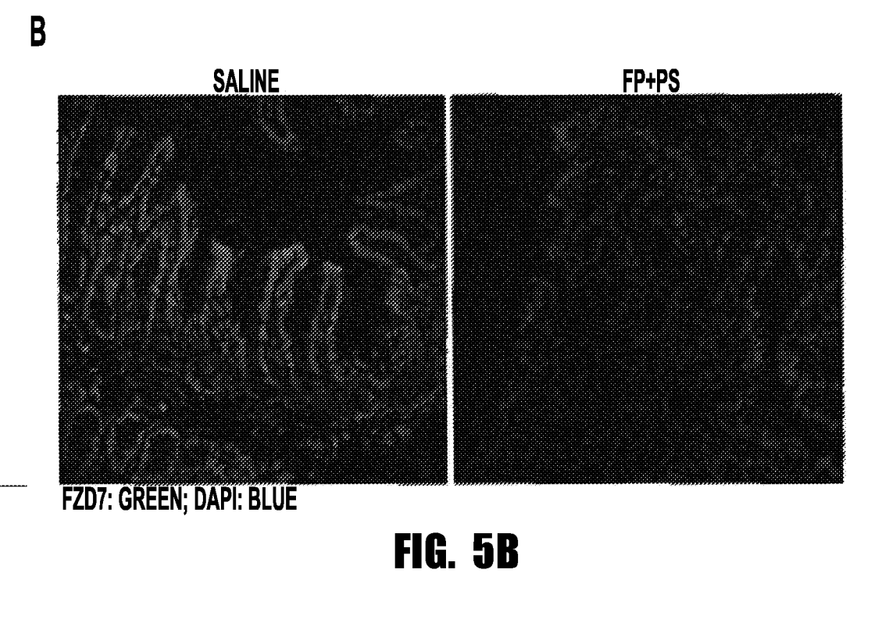

*F. prausnitzii* Plus Potato Starch Effect on Butyrate Transporter and Pathogen Receptors SLC5A8 transports butyrate via a Na+-dependent electrogenic process and its expression is downregulated in the absence of luminal butyrate. Cresci et al., J Parent Enteral Nutr, 37:763-774 (2013). We examined the expression of SLC5A8 via immunohistochemistry in proximal colon as a surrogate marker for butyrate presence due to FP and PS supplementation and found it maintained immunoreactive staining intensity, but that this intensity was depleted in saline treated mice (FIG. 5B).

Following colonization, CD toxins A and B (TcdA and TcdB) are released. For these toxins to exert their effects, they first bind to receptors in the intestine. Toll-like receptor 2 (TLR2) is a membrane protein that recognizes pathogen associated molecular patterns, particularly from gram positive bacteria. Frizzled class receptor 7 (FZD7) was recently identified as a physiologically relevant TcdB receptor in the colonic epithelium. Tao et al., Nature, 538:350-355 (2016). To determine whether CD colonization had the potential to exert a physiological response and subsequent infection by interacting with these pathogen receptors, we examined expression of TLR2 and FZD7 in proximal colon. Two time points were evaluated, 1-day and 5-day following CD exposure. Mice co-treated with FP+PS had reduced TLR2 mRNA expression 1-day following CD exposure compared to saline treated animals; and mRNA expression levels were similar at 5 days after CD between groups (FIG. 5A). Immunohistochemistry analysis showed FZD7 expression in colonic epithelium in saline treated mice 5 days after CD exposure, however FZD7 immunoreactive staining intensity was reduced in FP+PS treated mice (FIG. 5C).

Figure 6A:
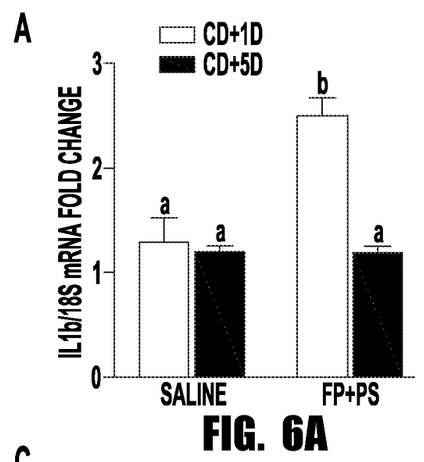
Figure 6B:
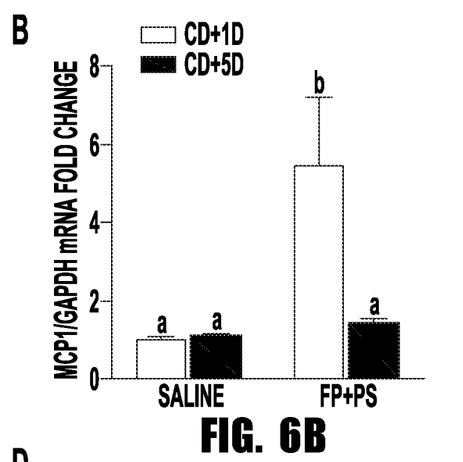
Figure 6C:
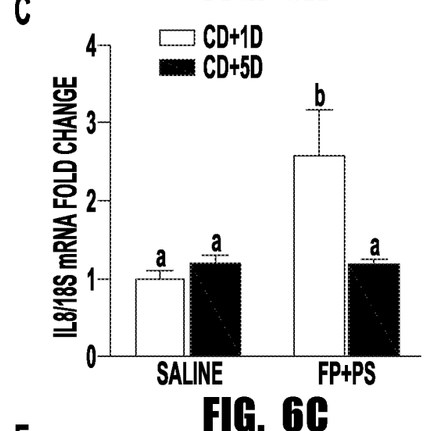
Figure 6D:
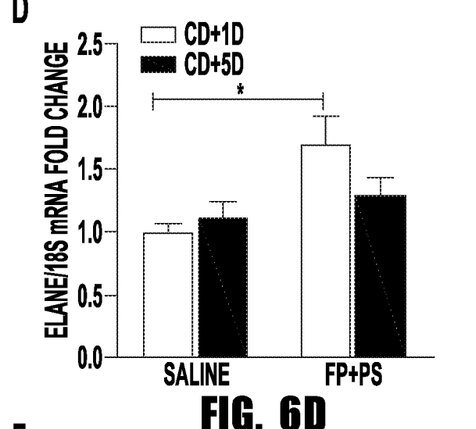
Figure 6E:
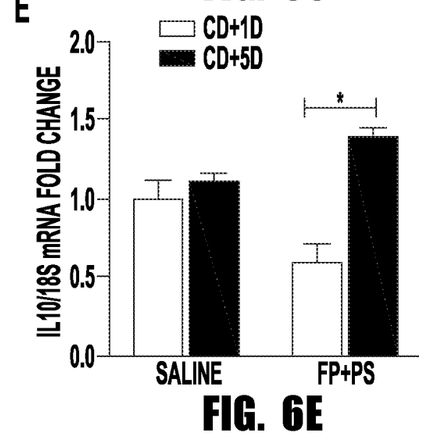
Figure 6F:
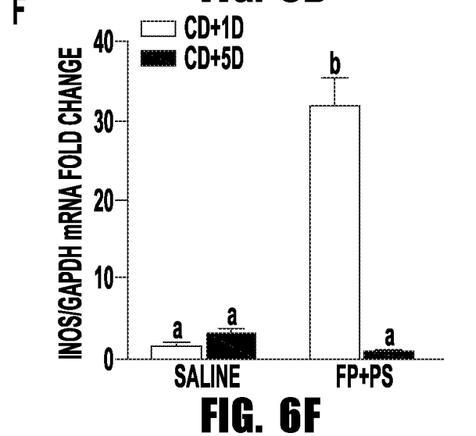

*F. prausnitzii* Plus Potato Starch Supported Immune Response Following CD Exposure An active immune response is required for bacterial clearance and tissue repair, and chemokine function is necessary for immune cell recruitment. Therefore we assessed cytokine/chemokine mRNA expression in proximal colon 1- and 5-days following CD exposure in saline and FP+PS treated mice. Mice in the saline group did not exhibit an induction in chemokines IL1β, MCP1 or IL8 at either time points. In contrast, mice co-supplemented with FP+PS exhibited an induction of these chemokines 1 day following CD exposure which were then reduced at day five (FIG. 6A-C). This chemokine induction was associated with an induction in ELANE mRNA and iNOS, markers for neutrophils and monocytes, respectively. Both ELANE and iNOS mRNA were blunted in saline treated mice at day 1 and did not change by day 5 (FIGS. 6D & F). While the anti-inflammatory cytokine IL-10 mRNA was low in the saline group at both time points, IL10 mRNA levels in the FP+PS group increased between day 1 and day 5 following CD exposure (FIG. 6E).

Discussion

We report for the first time the beneficial effects of oral supplementation of FP and PS against negative effects on colonic health induced by antibiotic and CD exposure in mice. While antibiotic treatment and a single CD exposure caused fecal bacterial overgrowth and colonization, clearance of bacterial burden was accelerated in mice supplemented with FP and PS. This was associated with protection of intestinal tight junction proteins, preservation of an anion exchanger, and acute induction and resolution of innate immune response.

Current theory suggests antibiotic-induced depletion of the dominant commensal bacterial phyla Bacteroidetes and Firmicutes, and increased Proteobacteria composition renders the intestinal environment susceptible to CD colonization. Butyrate-producing bacteria are found in Clostridia class of the Firmicutes phyla and depletion of butyrate-producing bacteria are noted to occur during CDI in both animals and humans. Staley et al., mBio 7:e01965-16 (2016).

Our studies were consistent with other reports in that antibiotic treatment induced overgrowth of enterococci and gram negative bacteria and allowed for CD colonization. Buffie et al., Infect Immun, 80:62-73 (2012). Other studies report clindamycin-induced bacterial overgrowth can last up to 28 days. Of note, while bacterial overgrowth and CD colonization occurred in all treatment groups, we found by day 3 following CD exposure, animals supplemented with a butyrate-producing bacteria and a butyrate-yielding prebiotic exhibited accelerated colonization recovery compared to those treated with saline. Additionally, CD colonization was not evenly distributed in each treatment group, indicating that animals appeared to respond individually to CD exposure. This is similar to reports found in human studies confirming the individuality of colonization patterns in vivo.

Butyrate is pleiotropic, known to support water and electrolyte absorption, immune function, and intestinal barrier integrity. Our prior work demonstrates supplementation with tributyrin, a triglyceride prodrug of butyrate, during broad spectrum antibiotic treatment in mice protects against intestinal losses of a sodium-coupled butyrate transporter, butyrate receptor, tight junction proteins and the $Na^+/H^+$ exchanger isoform 3 ($NHE_3$). Cresci et al., J Parent Enteral Nutr, 37:763-774 (2013). NHE3 is essential for intestinal absorption of sodium and water. CD toxin B (TcdB) was shown to inhibit NHE3 by dephosphorylation and redistribution of ezrin, a protein that anchors NHE3 to the cytoskeleton, resulting in loss of NHE3 from the apical membrane. Hayashi et al., J Gen Physiol, 123:491-504 Engevik, et al showed decreased NHE3 expression in colonic biopsies from patients with CDI, which associated with increased sodium content and alkalinity in CD positive stool. Engevik et al., Am J Physiol Gastrointes Liver Physiol 2015; 308: G497-G509 CD thrived in this environment demonstrating increased proliferation, while resident commensal bacteria C. butyricum, B. producta, or FP did not and were thus depleted.

Following CD colonization, secreted virulence factors, toxins A and B (TcdA and TcdB), bind to host receptors, are internalized into the enterocyte cytoplasm via endocytosis, and become enzymatically active. Intestinal epithelial barrier damage is attributed to actions of TcdA and TcdB. While we found animals supplemented with FP and PS still colonized with CD, we wanted to determine the potential for toxin virulence. As expected, expression of the newly identified TcdB receptor (FZD7) was highly expressed in the proximal colon of saline treated animals. However, TcdB expression was diminished in mice supplemented with FP and PS. This decreased TcdB receptor expression was associated with preservation of a sodium-coupled butyrate transporter, SLC5A8, and tight junction protein complexes in the proximal colon. Our prior work demonstrates that when commensal gut bacteria is depleted, butyrate transporter expression is also depleted; and that transporter expression returns to physiologic levels with the return of commensal bacteria and luminal butyrate which coincides with intact tight junction barrier. Taken together, we propose in our studies supplementation with butyrate-enhancing FP and PS maintained apical membrane expression of SLC5A8 and NHE3 and therefore physiologic colonic anion levels were maintained following CD exposure. By maintaining an environment unfavorable for CD to thrive, colonization clearance was accelerated; and due to lack of virulent toxin release, TcdB receptor was diminished and tight junction proteins were preserved in mice supplemented with FP and PS. FP and butyrate supplementation have both been associated with preservation of tight junction proteins. Sun et al., Mol Immunol., 63: 193-202 (2015).

While the severity of CDI can be influenced by the adaptive immune response, CDI onset, progression, and overall prognosis is impacted by innate immune responses to CD toxins. Clinically it is not the overall toxin burden that predicts poor outcomes, but rather the magnitude and duration of the inflammatory response triggered by CDI. Laval et al., Gut Microbes, 6:1-9 (2015). Demonstrated in mice with impaired innate immune capacity, following CD exposure animals were more vulnerable to CDI due to their inability to clear the initial infection and appropriately handle bacterial translocation across compromised intestinal epithelial barrier. El Feghaly et al., J Clin Dis, 56:1713-21 (2013).

Induction of an efficient innate immune response that involves release of inflammatory mediators and neutrophil recruitment is required for swift clearance of CD and protection against commensal bacterial translocation. Cell recruitment, or chemotaxis, is a highly regulated, receptor-mediated process in which cells migrate to chemokines, bacterial components and complement factors. Macrophages, mucosal expression and chemoattractant activity of TGFβ and IL-8 provide continuous recruitment of monocytes to the lamina propria in intestinal mucosa. Buonomo et al., Anaerobe, 14:79-84 (2016) Following infection, monocytes are recruited to the lamina propria of the intestine where they differentiate into major producers of iNOS. Most known as a microbicidal and inflammatory effector pathway in macrophages, iNOS is also found in other cell types including normal colonic epithelium. Inflammatory cytokines, hypoxia and microbial products can induce iNOS, while anti-inflammatory cytokines suppress iNOS gene transcription. Our studies found saline treated animals did not mount an immune response following CD exposure and colonization, and had associated losses of intestinal integrity at both time points evaluated. Conversely we show that while animals supplemented with FP and PS did colonize with CD, they also exhibited an early induction and then resolution of chemokines. These chemokine changes associated with clearance of bacterial burden and preservation of markers of intestinal integrity. The initial robust immune response must be adequately controlled in order to limit persistent and collateral tissue damage. A critical immunoregulatory cytokine, IL-10 limits and downregulates inflammatory responses. During lipopolysaccharide-induced innate immune response, macrophages and neutrophils are the major IL-10 producing cells. We found that while saline treated animals did not mount an immune response to chemokines, they also did not show any altered expression of anti-inflammatory cytokine IL-10. However, animals treated with FP and PS exhibited elevations in anti-inflammatory cytokine (IL10) at day 5, same time when pro-inflammatory mediators were resolved. Taken together, these effects tie into prior knowledge that butyrate and FP have known immunomodulatory and anti-inflammatory properties exhibiting protective effects against acute colitis. Pils et al., Inflamm Bowel Dis, 10:2038-2046 (2011); Miguel et al., mBIO, 6: e00300-15 (2015).

In summary, maintaining a balanced inflammatory response to counteract infection while limiting collateral tissue injury is likely beneficial during CD infection. We find protective effects of FP and PS against antibiotic-induced bacterial overgrowth and CD colonization following a single exposure in mice. These effects appear to be linked with an intact innate immune response that accelerates clearance of bacterial burden and protects against intestinal injury. As recurrent CD infection carries high morbidity and mortality, further studies investigating preventative strategies directed towards protecting the gut microbial ecosystem and intestinal integrity against antibiotic effects are warranted.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating or preventing overgrowth by pathogenic bacteria in a subject, comprising determining that the subject is deficient in butyrate and/or butyrate-producing bacteria in their gut microbiota, and administering a therapeutically effective amount of a butyrate-yielding prebiotic and a butyrate-producing bacteria to the subject.

2. The method of claim 1, wherein the prebiotic is starch.

3. The method of claim 1, wherein the pathogenic bacteria is *Clostridium difficile*.

4. The method of claim 1, wherein the subject is deficient in butyrate-producing bacteria.

5. The method of claim 4, wherein the butyrate-producing bacteria is *Faecalibacterium prausnitzii*.

6. The method of claim 1, wherein the subject is deficient in butyrate.

7. The method of claim 1, wherein the butyrate-producing bacteria is administered orally.

8. The method of claim 1, wherein the subject is a human.

9. The method of claim 1, wherein overgrowth by pathogenic bacteria is prevented.

10. The method of claim 1, wherein overgrowth by pathogenic bacteria is treated.

11. The method of claim 1, wherein the overgrowth by pathogenic bacteria is caused by antibiotic administration to the subject.

12. The method of claim 11, wherein the antibiotic is a fluoroquinolone antibiotic.

13. The method of claim 1, wherein the butyrate-producing bacteria is administered to the subject a plurality of times over a week or more of time.

14. The method of claim 1, wherein the butyrate-producing bacteria is administered in a pharmaceutically acceptable carrier.

15. The method of claim 14, wherein the pharmaceutically acceptable carrier is a capsule.

* * * * *